(12) United States Patent
Dernbach et al.

(10) Patent No.: US 6,586,641 B2
(45) Date of Patent: Jul. 1, 2003

(54) METHOD FOR THE DECOMPOSITION OF HIGH BOILING BY-PRODUCTS PRODUCED IN THE SYNTHESIS OF POLYHYDRIC ALCOHOLS

(75) Inventors: Matthias Dernbach, Dossenheim (DE); Detlef Kratz, Heidelberg (DE); Achim Stammer, Freinsheim (DE); Gerhard Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/169,001
(22) PCT Filed: Dec. 28, 2000
(86) PCT No.: PCT/EP00/13308
§ 371 (c)(1), (2), (4) Date: Jun. 26, 2002
(87) PCT Pub. No.: WO01/47848
PCT Pub. Date: Jul. 5, 2001

(65) Prior Publication Data
US 2003/0088131 A1 May 8, 2003

(30) Foreign Application Priority Data
Dec. 28, 1999 (DE) .......................................... 199 63 437

(51) Int. Cl.$^7$ .............................................. C07C 31/18
(52) U.S. Cl. ...................................... 568/853; 568/854
(58) Field of Search ................................. 568/853, 854

(56) References Cited

U.S. PATENT DOCUMENTS

| | | | |
|---|---|---|---|
| 3,259,662 A | 7/1966 | Munley | |
| 4,122,290 A | 10/1978 | Immel et al. | |
| 4,247,485 A | 1/1981 | Immel et al. | |
| 4,514,578 A | * | 4/1985 | Immel et al. |
| 4,594,461 A | * | 6/1986 | Merger et al. |
| 5,149,861 A | | 9/1992 | Merger et al. |
| 5,763,690 A | * | 6/1998 | Salek et al. |
| 6,018,074 A | | 1/2000 | Kratz et al. |
| 6,034,284 A | | 3/2000 | Doi et al. |
| 6,187,971 B1 | | 2/2001 | Kratz et al. |
| 6,344,592 B1 | * | 2/2002 | Iwamoto et al. |

FOREIGN PATENT DOCUMENTS

| | | |
|---|---|---|
| DE | 287 251 | 2/1991 |
| GB | 1535826 | 12/1978 |

OTHER PUBLICATIONS

Derwent Abst. 91–208981/29 of DD 287,251 (1991).

Organic Chemistry & Tech. Vysotskii et al., 599–600 (1977).

\* cited by examiner

Primary Examiner—Michael L. Shippen
(74) Attorney, Agent, or Firm—Keil & Weinkauf

(57) ABSTRACT

A process is provided for increasing the yield in the preparation of polyhydric alcohols obtained from methylolated alkanals by hydrogenation, wherein derivatives of these alcohols are decomposed by adding 5 ppm to 1% by weight, preferably 100 to 1000 ppm, of a suitable acid to an anhydrous mixture containing these derivatives, heating the mixture to temperatures of 100 to 300° C. and then separating off the polyhydric alcohol by distillation. This process makes it possible simply and efficiently to decompose compounds which boil above the polyhydric alcohol and are unwanted by-products of its synthesis.

17 Claims, No Drawings

METHOD FOR THE DECOMPOSITION OF HIGH BOILING BY-PRODUCTS PRODUCED IN THE SYNTHESIS OF POLYHYDRIC ALCOHOLS

The present invention relates to the field of industrial organic chemistry. More precisely, the present patent application relates to a process in which polyhydric alcohols prepared by the condensation of formaldehyde with higher aldehydes, followed by hydrogenation, are freed of higher-boiling substances formed in the preparation.

When reacted with formaldehyde in the presence of bases, aldehydes which have at least one acidic hydrogen atom in the α-position to the carbonyl group first form methylolated aldehydes by simple aldol condensation. These methylolated aldehydes then serve as starting substances for the preparation of said polyhydric alcohols by reduction of the aldehyde group to the alcohol group.

Different process variants can be used here, according to how this reduction is carried out.

Firstly, there is the inorganic Cannizzaro process, where formaldehyde is reacted with the higher aldehyde in the presence of stoichiometric amounts of an inorganic base, generally NaOH, $Ca(OH)_2$ or $Ba(OH)_2$. After the condensation, the methylolated aldehyde then reacts with more formaldehyde under the influence of the base in a so-called crossed Cannizzaro reaction to give the polyhydric alcohol and formic acid, in the form of its salt, by disproportionation. The production of this formate is a disadvantage because it cannot be re-used and has to be disposed of. This pollutes the environment; in addition, one mole of formaldehyde is lost per mole of alcohol obtained.

In a widely used variant, the so-called organic Cannizzaro process, the inorganic base is replaced with a tertiary amine, generally a trialkylamine. This amine is also used in stoichiometric amounts. The reaction proceeds in the same way as in the inorganic Cannizzaro process except that the trialkylammonium formate of the amine used is formed instead of an alkali metal or alkaline earth metal formate. This organic Cannizzaro reaction proceeds without the formation of alkali metal salts, thereby simplifying the work-up. Also, it is possible to work up the trialkylammonium formate further and recover the bound amine, which is then re-used in the reaction. Different variants of this work-up of trialkylammonium formates are described in patent applications EP-A-289 921, WO 97/17313 and DE-A-198 48 568.

Finally, it is also known to prepare polyhydric alcohols by the so-called hydrogenation process. Here, the condensation reaction between formaldehyde and higher aldehyde is carried out in such a way that the reaction stops at the methylolated alkanal stage. This is achieved by adding only catalytic amounts of a tertiary amine, which here again is generally a trialkylamine. The methylolated alkanals are reduced by hydrogenation in a manner known per se to give the desired polyhydric alcohol.

Different reaction variants of this hydrogenation process can be found for example in patent applications DE-A-25 07 461, DE-A-27 02 582 and DE-A-28 13 201. A particularly suitable process is disclosed in WO 98/28253. Here, a complete conversion of the educts to methylolated alkanals is achieved by an efficient and comparatively simple process for separation of the reaction mixture initially obtained, and recycling of the resulting fractions. The alkanal obtained is then hydrogenated in a manner known per se. In a first reaction step, the starting aldehyde is reacted with 2 to 8 times the amount of formaldehyde in the presence of approx. 5 to 10 mol % of a trialkylamine, preferably trimethylamine.

When the reaction is complete, the mixture obtained is then separated by distillation to give a bottom stream containing the alkanal and a distillate stream containing unreacted educts. Alternatively, the crude reaction mixture can also be separated into an aqueous phase and an organic phase, the latter containing unconverted reaction products. The distillate stream or organic phase is recycled into the first step, so only a small part of the starting compounds is lost. The bottom product obtained after distillation or the aqueous phase obtained after phase separation is then subjected to an appropriate catalytic or thermal treatment in order to effect a complete conversion of by-products (arising due to incomplete reaction or elimination) to the desired alkylolated alkanal. This is followed by another distillation, where a top product is withdrawn and recycled into the first reaction step. The bottom product obtained after this last distillation is then hydrogenated to polyhydric alcohol.

The crude product mixtures obtained by the hydrogenation process have a higher product content than crude mixtures obtained by the Cannizzaro process. The work-up of the mixtures obtained by this process is therefore fundamentally different from that of the mixtures obtained by the hydrogenation process.

The only common feature of the two processes is that the polyhydric alcohol is freed, by distillation, of components which are more volatile than said alcohol (so-called low-boiling components) or less volatile than said alcohol (so-called high-boiling components). Low-boiling components here are especially water, methanol and, when using an amine as catalyst, the free amine and also trialkylammonium formate.

The high-boiling components are often compounds which are derivatives of the polyhydric alcohol prepared and which are formed therefrom by reaction with e.g. formaldehyde, methanol or a further molecule of the alcohol prepared. The following compounds are examples of typical higher-boiling secondary components in the case where the trihydric alcohol trimethylolpropane (TMP), $C_2H_5C(CH_2OH)_3$, is synthesized from formaldehyde and n-butyraldehyde in the presence of catalytic amounts of trialkylamine: so-called di-TMP, $[C_2H_5C(CH_2OH)_2CH_2]_2O$, linear bis-TMP-formal, $[C_2H_5C(CH_2OH)_2CH_2O]CH_2$, cyclic TMP-formal:

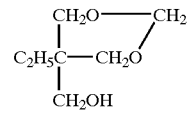

the condensation product of TMP, formaldehyde and methanol (TMP-FA-MeOH), the acetal of dimethylolbutanal with trimethylolpropane (DMB-TMP-acetal) and TMP formates, i.e. formic acid monoesters of trimethylolpropane.

It is obvious that the formation of these high-boiling components containing TMP units is undesirable because they markedly reduce the yield of desired product. However, the formation of these high-boiling components can never be completely suppressed, even when caution is exercised in carrying out the reaction. To increase the yield, it is desirable to decompose these high-boiling components. Various processes with this aim are disclosed in the literature.

Patent DE-P-287 251 describes the decomposition of high-boiling components, especially bis-TMP-formal, in solutions recovered after distillative separation of the TMP obtained in the preparation of TMP by the inorganic Cannizzaro process. The resulting bottom product is then treated with 1 to 10% by weight of a strong or moderately strong acid, for example sulfuric acid or phosphoric acid, and then heated for 6 minutes to 10 hours at temperatures of 80 to 180° C. This treatment cleaves some of the high-boiling components derived from TMP. For example, the addition of 5% by weight of concentrated sulfuric acid to a crude high-boiling mixture and heating at 130° C. for 12 minutes, with subsequent distillation to recover TMP, effects a complete decomposition of bis-TMP-formal and hence increases the yield of TMP, but unwanted cyclic TMP-formal (not previously present) is also formed in appreciable amounts.

In SU 335141, whose disclosure is practically identical to that of the article "The Soviet Chemical Industry", 1977, 9:8, pages 599 to 600, a process is disclosed in which the low-boiling fraction of TMP obtained by the inorganic Cannizzaro process is worked up by adding 1 to 8% by weight of sulfuric acid and introducing superheated steam at a temperature of 180 to 200° C. into the solution with a bottom temperature of 170 to 180° C. TMP is then distilled from this bottom product. An increase in the overall yield of TMP can thus be achieved by hydrolysis of the cyclic TMP-formal and the TMP formates, the indicated yield of TMP in the decomposition step being 18 to 20%. However, an unwanted higher-boiling product is also formed in a yield of 53 to 55%.

Finally, U.S. Pat. No. 3,259,662 discloses another process in which a crude TMP solution obtained by the inorganic Cannizzaro process is distilled with the addition of acid, the latter being added during the distillation of the lower-boiling components, after the removal of formaldehyde. The TMP is then distilled from the high-boiling components, the pH being rendered alkaline at the bottom of the column. The TMP recovered by this process is odorless.

However, the processes described above are not suitable for working up TMP obtained by the hydrogenation process, or other polyhydric alcohols. The reaction mixture to be worked up is markedly different from reaction discharges of the Cannizzaro process. It contains no alkali metal or alkaline earth metal ions and only small amounts of tertiary amine or the corresponding trialkylammonium formate. Simple dehydration of the alcohol obtained after hydrogenation gives a crude alcohol mixture with a product content of 80 to 85%. In contrast to crude mixtures obtained by the Cannizzaro process (organic or inorganic), pure TMP can be obtained from the dehydrated crude solutions by means of distillation steps. Small amounts of impurities have to be separated off. The addition of large amounts of acid, the additional introduction of steam, for instance, and additional separation steps are undesirable because, although an improvement in the yield by decomposition of the TMP adducts is very desirable, the amount of these adducts is smaller with the hydrogenation process than with the Cannizzaro process and therefore does not justify high expenditure.

It is therefore an object of the present invention to provide a process for improving the yield of polyhydric alcohol prepared by the hydrogenation process. This process should be efficient and not expensive, but at the same time should improve the yield of polyhydric alcohol to the extent that its use with the hydrogenation process is justified.

We have found that this object is achieved by a process for increasing the yield in the preparation of polyhydric alcohols obtained from methylolated alkanals by hydrogenation, wherein derivatives of these alcohols are decomposed by adding 5 ppm to 1% by weight, preferably 100 to 1000 ppm, of a suitable acid to a mixture containing these derivatives, heating the mixture to temperatures of 100 to 300° C. and then separating off the polyhydric alcohol by distillation.

It has been found, surprisingly, that by adding small amounts of acid to the fraction containing high-boiling components, obtained in the preparation of polyhydric alcohols by the hydrogenation process, and heating to high temperatures of up to 300° C., a marked decomposition of the high-boiling components derived from the polyhydric alcohol in question can be achieved. This simple process affords an increase in yield of up to several percent. In the process according to the invention, the synthesis of the polyhydric alcohols, i.e. the condensation reaction between formaldehyde and higher aldehyde in the presence of catalytic amounts of tertiary amine, followed by catalytic hydrogenation of this mixture, is carried out as described in the literature. Examples of different process variants can be found in patent applications DE-A-25 07461, DE-A-27 02 582 and DE-A-28 13 201, which have already been cited above. The process according to the invention is particularly suitable for the removal of high-boiling components from mixtures prepared by the process described in WO 98/28253. A short description of this process was given earlier. Work-up then proceeds in conventional manner, as described in the literature, generally by separation of the water and subsequent distillation.

Within the framework of the present invention, good results have been achieved with crude alcohol mixtures which have first been dehydrated by the conventional processes, it being desirable to have water contents of $\leqq 5\%$ by weight or, preferably, $\leqq 0.5\%$ by weight.

The amount of acid which, according to the present invention, is added to the dehydrated mixture in order to decompose the high-boiling components is much smaller than in the processes available in the state of the art, which all relate to the Cannizzaro process. According to the invention, 5 ppm to 1% by weight of acid is used, the preferred amounts being 100 to 1000 ppm. It has frequently been observed that the addition of amounts of acid in excess of the range indicated here causes the mixture to polymerize on heating or during the distillation serving to separate off the alcohol formed.

According to the invention, the acids which can be used are conventional strong or moderately strong acids known to those skilled in the art. Examples are sulfuric acid, sulfurous acid, hydrohalic acids such as HCl, in either gaseous or aqueous form, phosphoric acid, sulfonic acids such as arylsulfonic and alkylsulfonic acids, acidic ion exchangers, phosphorous acid, boric acid, alkanoic acids and carbonic acid. It is preferable to use phosphoric acid.

The cleavage of high-boiling components according to the invention takes place at temperatures of 100 to 300° C., preferably 150 to 280° C. and particularly preferably 180 to 250° C. The chosen residence times in respect of the TMP feed range from 0.1 to 20 hours, preferably from 0.5 to 5 hours.

The process according to the invention is not markedly dependent on pressure. The decomposition can be carried out under reduced pressure, under atmospheric pressure or under an applied external pressure. The reaction is preferably carried out below atmospheric pressure, i.e. at 1–950 mbar, preferably 10–100 mbar and particularly preferably 10–50 mbar. It is possible to work without an inert gas atmosphere or with e.g. an inert argon or nitrogen atmosphere.

The abovementioned reaction conditions used for decomposing the high-boiling components according to the present invention can be employed at different times and at different stages of the process during the work-up of the dehydrated crude alcohol mixture. On the one hand, for example, it is possible, in the distillative separation of the product alcohol from the high-boiling components, simply to add the requisite amount of acid to the bottom product and otherwise to observe, in the distillation, the conditions necessary for cleavage of the high-boiling components, as described above, thereby increasing the amount of product alcohol in the mixture which distils off.

It is also possible to separate the high-boiling fraction from the product and the low-boiling components by means of suitable measures, for example by distillation. In a separate step, the process according to the invention is then carried out on the high-boiling fraction, and the product alcohol obtained by decomposition of the high-boiling components is distilled off. This product alcohol can then be isolated as such, optionally after further purification by distillation. It is also possible, however, to recycle the distillate into one of the previous distillation steps in which the product alcohol is obtained in pure form by distillation. The decomposition reaction can take place e.g. in a tubular reactor or a stirred tank.

The decomposition of high-boiling components according to the invention can be carried out particularly satisfactorily in combination with the process described in the German patent application entitled "Verfahren zur Reinigung von durch Hydrierung erhaltenem Trimethylolpropan durch kontinuierliche Destillation", reference no. 199 63 435.1 (Applicant: BASF AG). In said process, trimethylolpropane (TMP) originating from the hydrogenation of 2,2-dimethylolbutanal is worked up by distillation, water and other low-boiling components, such as methanol, trialkylamine and also trialkylammonium formate, being separated by distillation, in the first step, from the mixture obtained after hydrogenation. This gives a mixture containing TMP, high-boiling components and part of the low-boiling components and, optionally after a further treatment for the conversion and separation of by-products, the TMP and low-boiling components are separated from the high-boiling components by distillation and then worked up. The high-boiling fraction can be discarded or partially recycled into the reaction. The disclosure of the abovementioned patent application is included in the present patent application by way of reference.

If, in the process disclosed in said cited patent application, acid in the concentrations according to the invention is added to the bottom product during the separation of the TMP and other low-boiling components from the high-boiling components, and the conditions according to the invention are maintained during the distillation, the yield can be increased. Another possibility, however, is for the high-boiling bottom product after distillation to be treated separately by the process according to the invention and for the resulting TMP to be distilled off.

In another preferred embodiment of the present invention, an anhydrous dialkylamine is added to the crude discharge after dehydration in order to decompose formates of the polyhydric alcohol to give the corresponding alcohol and formamide. Such a process is disclosed in the German patent application entitled "Verfahren zur Umwandlung von bei der Trimethylolalkan-Herstellung anfallenden Trimethylolalkanformiat", reference no. 199 63 444.0 (Applicant: BASF AG). This process is also an integral part of the present patent application and is included therein by way of reference. The decomposition of the formates is then followed by the work-up according to the invention with the addition of acid.

The process is applicable to any polyhydric alcohols which can be prepared by condensing formaldehyde with higher aldehydes, in the presence of catalytic amounts of trialkylamine, and then hydrogenating the products. Practically any alkanals with an acidic hydrogen atom in the α-position to the carbonyl group are suitable higher aldehydes. Starting materials which can be used are aliphatic aldehydes having from 2 to 24 C atoms which can be linear or branched or can also contain alicyclic groups. Other suitable starting materials are araliphatic aldehydes, provided that they contain a methylene group in the α-position to the carbonyl group. In general, aralkylaldehydes having from 8 to 24 C atoms, preferably from 8 to 12 C atoms, for example phenylacetaldehyde, are used as starting materials. Aliphatic aldehydes having from 2 to 12 C atoms are preferred, examples being 3-ethyl-, 3-n-propyl-, 3-isopropyl-, 3-n-butyl-, 3-isobutyl-, 3-sec-butyl- and 3-tert-butyl-butanal and the corresponding n-pentanals, n-hexanals and n-heptanals; 4-ethyl-, 4-n-propyl-, 4-isopropyl-, 4-n-butyl-, 4-isobutyl-, 4-sec-butyl- and 4-tert-butyl-pentanals, -n-hexanals and -n-heptanals; 5-ethyl-, 5-n-propyl-, 5-isopropyl-, 5-n-butyl-, 5-isobutyl-, 5-sec-butyl- and 5-tert-butyl-n-hexanals and -n-heptanals; 3-methylhexanal and 3-methylheptanal; 4-methylpentanal, 4-methylheptanal, 5-methylhexanal and 5-methylheptanal; 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentyl-aldehyde; $C_2$ to $C_{12}$ n-alkanals are particularly preferred.

Particularly preferred polyhydric alcohols within the framework of the present invention are trimethylolethane, trimethylolpropane, trimethylolbutane, neopentyl glycol and pentaerythritol, trimethylolpropane being very particularly preferred.

The invention will now be illustrated in the Examples which follow.

EXAMPLE 1

Crude TMP was prepared as follows:

An apparatus consisting of two heatable stirred tanks with an overall capacity of 72 l, interconnected by overflow tubes, was charged continuously with fresh aqueous formaldehyde solution (4300 g/h) in the form of a 40% aqueous solution, and n-butyraldehyde (1800 g/h), and with fresh trimethylamine as catalyst (130 g/h) in the form of a 45% aqueous solution. The reactors were heated to a constant temperature of 40° C.

The discharge was passed directly into the top of a falling film evaporator with attached column (superheated steam at 11 bar), where it was separated by distillation under atmospheric pressure into a low-boiling top product, essentially containing n-butyraldehyde, ethylacrolein, formaldehyde, water and trimethylamine, and a high-boiling bottom product.

The top product was continuously condensed and recycled into the reactors described above.

The high-boiling bottom product from the evaporator (approx. 33.5 kg/h) was treated continuously with fresh trimethylamine catalyst (50 g/h in the form of a 45% aqueous solution) and transferred to a heatable, packed tubular reactor with an empty volume of 12 l. The reactor was heated to a constant temperature of 40° C.

The discharge from the secondary reactor was passed continuously into the top of another distillation device for separation of the formaldehyde (superheated steam at 11 bar), where it was separated by distillation into a low-boiling top product, essentially containing ethylacrolein, formaldehyde, water and trimethylamine, and a high-boiling bottom product. The low-boiling top product (27 kg/h) was continuously condensed and recycled into the first stirred tank, while the high-boiling bottom product was collected.

In addition to water, the resulting bottom product contained essentially dimethylolbutyraldehyde, formaldehyde and traces of monomethylolbutyraldehyde. This bottom product was then subjected to continuous hydrogenation. This was done by hydrogenating the reaction solution at 90 bar and 115° C. in a primary reactor by the loop/trickle method and in a downstream secondary reactor by the loop method. The catalyst was prepared analogously to D of DE 198 09 418. It contained 24% of CuO, 20% of Cu and 46% of $TiO_2$. The apparatus used consisted of a heated secondary reactor with a length of 10 m (internal diameter: 25 mm). The loop throughput was 25 l/h of liquid and the reactor feed was adjusted to 4 kg/h, corresponding to a hydrogenation discharge of 4 kg/h.

The mixture obtained after hydrogenation was then freed of water and trimethylamine according to the German patent application entitled "Verfahren zur Reinigung von durch Hydrierung erhaltenem Trimethylolpropan durch kontinuierliche Destillation", reference no. 199 63 435.1 (Applicant: BASF AG). The crude mixture was first introduced into the column for low-boiling components, the dehydration being carried out at 400 mbar and 180° C. The feed entered the column in the middle. The reflux ratio was adjusted to 0.3. The bottom discharge obtained (1.1 kg/h) had the following composition according to gas chromatography:

TABLE 1

| 2-Ethyl-1,3-propanediol | Cyclic TMP-formal | TMP | TMP mono-formate | TMP—FA—MeOH | DMB—TMP-acetal |
|---|---|---|---|---|---|
| 0.8 | 0.6 | 82.6 | 7.7 | 1.7 | 2.2 |

From this bottom discharge in a packed column, 1.15 kg/h of TMP were then distilled off at the top of the column under a pressure of 20 mbar and at a top temperature of 184° C. The bottom temperature was 230° C. 66 g/h of the bottom product were extracted at regular intervals. During the distillation, 1 ml of 85% phosphoric acid was added to the bottom product every 3 days, thereby maintaining an acid concentration of approx. 90 to 530 ppm in the bottom product. 1.07 kg/h of crude TMP were distilled off at the top. According to gas chromatographic analysis (with prior silylation of the TMP with methylsilyltrifluoroacetamide), the composition of this product was as follows:

TABLE 2

| 2-Ethyl-1,3-propanediol | Cyclic TMP-formal | TMP | TMP monoformate | TMP—FA—MeOH |
|---|---|---|---|---|
| 1.4 | 1.2 | 90.2 | 4.1 | 0.8 |

A total of 965 g/h of TMP could thus be distilled off at the top.

Comparative Example 1

The distillation was carried out as described in Example 1 except that no phosphoric acid was added and 1.02 kg/h of TMP were withdrawn. According to gas chromatographic analysis, the product obtained had the following composition:

TABLE 3

| 2-Ethyl-1,3-propanediol | Cyclic TMP-formal | TMP | TMP monoformate | TMP—EA—MeOH |
|---|---|---|---|---|
| 0.7 | 0.9 | 89.8 | 5.5 | 1.0 |

A total of 916 g/h of TMP could thus be distilled off at the top.

EXAMPLE 2

1000 g of a crude TMP discharge, prepared and dehydrated as described in Example 1, were rectified batchwise at 2 mbar over a filled column with a height of 20 cm and a diameter of 2.9 cm. Before the distillation began, 250 ppm of phosphoric acid were added in the form of an 85% aqueous solution. The initial temperature of the bottom product was 180° C. and was gradually raised to 235° C. The following three fractions were obtained:

18 g of low-boiling components (top temperature: 60 to 145° C.)

915 g of main fraction (top temperature: 148 to 165° C.)

40 g of residue

Gas chromatographic analysis of the main fraction showed that a total of 828 g of TMP could be distilled over.

EXAMPLE 3

The procedure was as described in Example 2 except that 1000 ppm of $H_3PO_4$ were added in the form of an 85% aqueous solution. 3 fractions were again obtained and these were withdrawn at the same temperatures as in Example 2 to give:

17 g of low-boiling components 932 g of main fraction 20 g of residue

Gas chromatographic analysis of the main fraction showed that a total of 815 g of TMP could be distilled over.

Comparative Example 2

The procedure was as described in Example 2 except that no phosphoric acid was added. 3 fractions were again obtained and these were withdrawn at the same temperatures as in Example 2 to give:

31 g of low-boiling components 860 g of main fraction 100 g of residue

Gas chromatographic analysis of the main fraction showed that 797 g of TMP could be distilled over.

EXAMPLE 4

1000 g of dehydrated crude TMP discharge prepared according to Example 1 were treated with 41 g of diethylamine and stirred at 55° C. for 1 h. The excess diethylamine was then removed by distillation and 250 ppm of $H_3PO_4$ (85% aqueous solution) were added to the remaining mixture.

The mixture was then distilled analogously to Example 2. 3 fractions were again obtained and these were withdrawn at the same temperatures as in Example 2:

57 g of low-boiling components 890 g of main fraction 43 g of residue

GC analysis of the main fraction showed that a total of 848 g of TMP could be distilled over in the main fraction.

EXAMPLE 5

400 g of the high-boiling stream extracted from the bottom of the column as in Example 1 were rectified batchwise using a packed column with a height of 20 cm and a diameter of 2.9 cm, the pressure being 2 mbar. 125 ppm of phosphoric acid were added to the bottom product in the form of an 85% aqueous solution. The bottom temperature started at 180° C. and was raised to 235° C. This gave 152 g of a distillate, withdrawn at a top temperature of 160 to 190° C., and at the same time 240 g of residue. Gas chromatographic analysis of the distillate showed that a total of 104 g of TMP could be distilled over.

EXAMPLE 6

The procedure was as described in Example 5 except that the amount of 85% phosphoric acid added was 625 ppm. This gave 206 g of distillate, withdrawn at a top temperature of 160 to 170° C., and 186 g of residue. Gas chromatographic analysis of the distillate showed that a total of 158 g of TMP could be distilled over. A vitreous solidified residue remained.

Comparative Example 3

The procedure was as described in Example 5 except that no phosphoric acid was added. 73 g of distillate were withdrawn at a top temperature of 150 to 195° C. and the amount of residue obtained was 320 g. Gas chromatographic analysis of the distillate showed that a total of 55 g of TMP could be distilled over.

We claim:

1. A process for increasing the yield in the preparation of polyhydric alcohols obtained from methylolated alkanals by hydrogenation, wherein derivatives of these alcohols are decomposed by adding 5 ppm to 1% by weight, of a suitable acid to a mixture containing these derivatives, heating the mixture to temperatures of 150 to 280° C. and then separating off the polyhydric alcohol by distillation.

2. A process as claimed in claim 1, wherein the temperature is from 180 to 250° C.

3. A process as claimed in claim 1, wherein 100 to 1000 ppm of a suitable acid are added.

4. A process as claimed in claim 1, wherein the reaction is carried out under superatmospheric pressure, under atmospheric pressure or under reduced pressure.

5. A process as claimed in claim 1, wherein the mixture containing the derivatives of the polyhydric alcohols only contains small amounts of water.

6. A process as claimed in claim 5, wherein the mixture contains ≦5% by weight of water.

7. A process as claimed in claim 5, wherein the mixture contains ≦5% by weight of water.

8. A process as claimed in claim 1, wherein the residence time in respect of the alcohol feed is 0.1 to 20 hours.

9. A process as claimed in claim 8, wherein the residence time is 0.5 to 5 hours.

10. A process as claimed in claim 1, wherein a strong or moderately strong acid is used.

11. A process as claimed in claim 10, wherein phosphoric acid is used.

12. A process as claimed in claim 1, wherein the polyhydric alcohols are selected from the group consisting of trimethylolethane, trimethylolpropane, trimethylobutane, neopentyl glycol and pentaerythritol, trimethylolpropane being particularly preferred.

13. A process as claimed in claim 1, wherein the polyhydric alcohols are selected from the group consisting of trimethylolethane, trimethylolpropane, trimethylolbutane, neopentyl glycol and pentaerythritol.

14. A process as claimed in claim 13, wherein the polyhydric alcohols is trimethylolpropane.

15. A process as claimed in claim 1, wherein a secondary amine is added to the mixture before the acid is added.

16. A process as claimed in claim 1 which is carried out on mixtures from which the polyhydric alcohol has not yet been removed by distillation.

17. A process as claimed in claim 1 which is carried out on mixtures from which the polyhydric alcohol has already been removed by distillation.

* * * * *